US00PP36368P2

(12) United States Plant Patent
van Kessel

(10) Patent No.: US PP36,368 P2
(45) Date of Patent: Dec. 31, 2024

(54) ***SARRACENIA* PLANT NAMED '23CF101'**

(50) Latin Name: ***Sarracenia* hybrid**
Varietal Denomination: 23CF101

(71) Applicant: Carni Flora B.V., Aalsmeer (NL)

(72) Inventor: Justin van Kessel, Aalsmeer (NL)

(73) Assignee: Carni Flora BV (NL)

( * ) Notice: Subject to any disclaimer, the term of this patent is extended or adjusted under 35 U.S.C. 154(b) by 0 days.

(21) Appl. No.: 18/661,948

(22) Filed: May 13, 2024

(51) Int. Cl.
*A01H 5/12* (2018.01)
*A01H 6/00* (2018.01)

(52) U.S. Cl.
USPC ..... Plt./477

(58) Field of Classification Search
USPC ..... Plt./477
See application file for complete search history.

*Primary Examiner* — Susan McCormick Ewoldt
*Assistant Examiner* — Zachariah Allan Kay
(74) *Attorney, Agent, or Firm* — Cassandra Bright

(57) ABSTRACT

A new and distinct cultivar of *Sarracenia* plant named '23CF101' is disclosed, characterized by a uniquely elongated pitcher topped with a large, round, asymmetric hood. Young pitchers and hood are light-green, turning into a burgundy-red hood and a red-veined green pitcher that becomes almost fully green downwards. The new variety is a *Sarracenia*, with uses as both an indoor and outdoor ornamental plant.

4 Drawing Sheets

Latin name of the genus and species: *Sarracenia* hybrid.
Variety denomination: '23CF101'.

BACKGROUND OF THE INVENTION

This application relates to a new cultivar of *Sarracenia*. The new variety is the product of a planned breeding program to develop distinct, better performing new *Sarracenia* varieties. The seed parent is the unpatented variety *Sarracenia* 'Smoorii'. The pollen parent is the unpatented variety *Sarracenia* 'Catesbaei'. The crossing resulting in the new variety was made in 2016, at a nursery in Aalsmeer, the Netherlands.

*Sarracenia* '23CF101' was selected by the inventor as an interesting new cultivar in 2019 at the same nursery in Aalsmeer, the Netherlands.

Asexual reproduction of the new cultivar '23CF101' was first performed at a tissue lab in the Netherlands by tissue culture in April of 2019. Through subsequent asexual propagation, approximately 4 generations have been reproduced, which have shown that the unique features of this cultivar are stable and reproduced true to type.

SUMMARY OF THE INVENTION

The cultivar '23CF101' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of '23CF101.' These characteristics in combination distinguish '23CF101' as a new and distinct *Sarracenia* cultivar:

1. Colors of the pitcher and hood: young pitchers and hood are light-green, turning into a burgundy-red hood and a red-veined green pitcher that becomes almost fully green downwards.

2. Big, round, asymmetric hood.
3. Elongated pitcher topped with a round, asymmetric hood.

PARENT COMPARISONS

Plants of the new cultivar '23CF101' are similar to the seed parent variety, in many horticultural characteristics. However, the new variety, '23CF101' differs in the following characteristics:

1. The hood of the new variety stands fully upright, while the hood of the seed parent is slightly bent over the pitcher.
2. The hood of the new variety is larger than the hood of the seed parent.
3. Pitchers of the new variety have a dent halfway, while the pitchers of the seed parent have no dent.

Plants of the new cultivar '23CF101' are similar to the pollen parent variety, in many horticultural characteristics. However, the new variety, '23CF101' differs in the following characteristics:

1. The hood of the new variety is more rounded, while the hood of the pollen parent is more pointed.
2. Young pitchers of the new variety are light-green, while the young pitchers of the pollen parent are fluorescent green.
3. The pitcher netting of the new variety does not extend to the base. The pitcher netting of the pollen parent extends all the way down the pitcher.

COMMERCIAL COMPARISONS

The new variety can be compared to the commercial variety *Sarracenia* 'Stingray', unpatented. However, the new variety, '23CF101' differs from 'Stingray' in the following characteristics:

1. The hood of the new variety stands fully upright, while the hood of this comparator is slightly bent over the pitcher.

2. The top of the mature pitcher and hood of the new variety is a dark, burgundy-red color. The top of the mature pitcher and hood of this comparator is a light, pink-red color.

'23CF101' can be compared with the commercial variety *Sarracenia*. 'Abandoned Hope', unpatented. However, the new variety, '23CF101' differs from 'Abandoned Hope' in the following characteristics:

1. The hood of the new variety stands fully upright, while the hood of this comparator is slightly bent over the pitcher.
2. Pitchers of the new variety are not as long as pitchers of this comparator.
3. Mature hoods of the new variety become a fully intense burgundy-red, while mature hoods of this comparator are sometimes red, only at the bend of hood and pitcher.

BRIEF DESCRIPTION OF THE PHOTOGRAPHS

The accompanying photograph in FIG. 1 illustrates in full color a typical plant of '23CF101' grown in a glass greenhouse in Aalsmeer, the Netherlands. The plant is in a 12-cm pot, approximately one year old.

Figure 1:
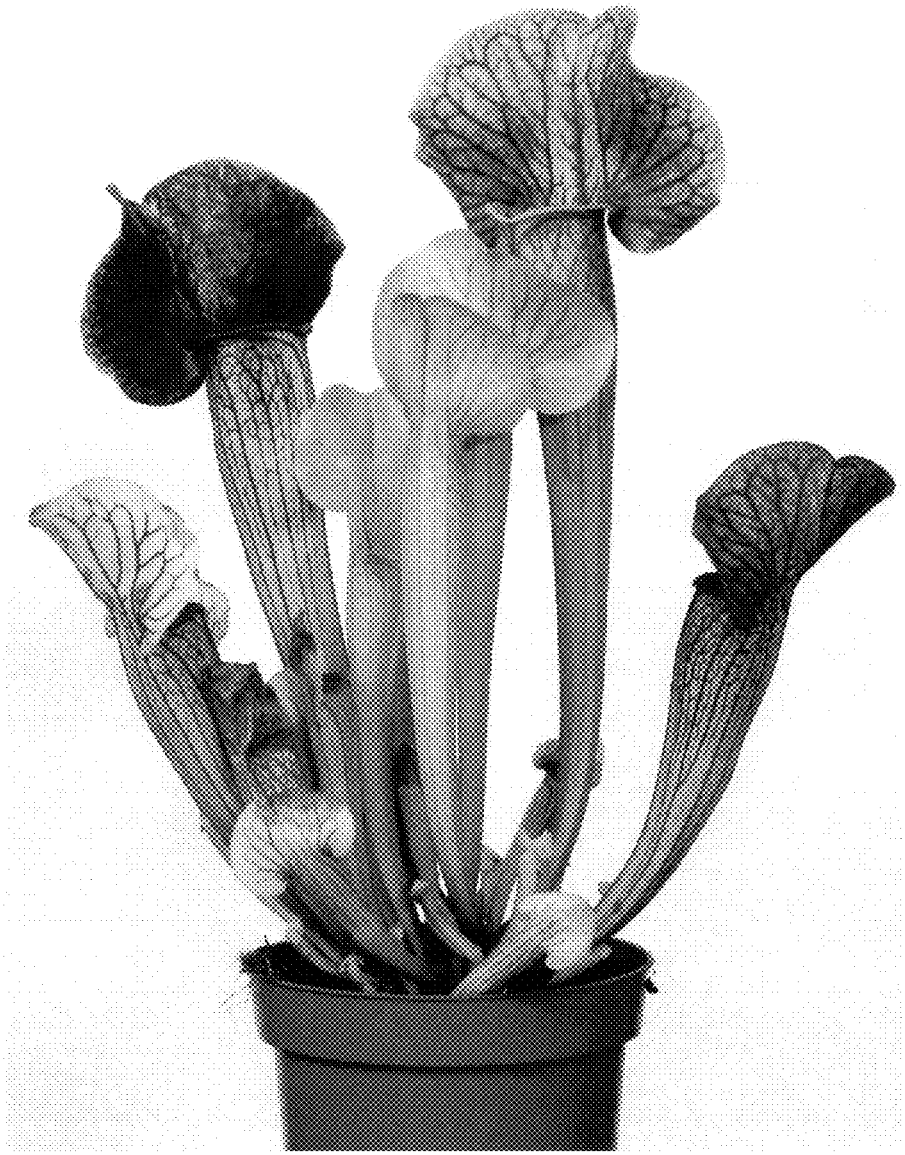
Figure 2:
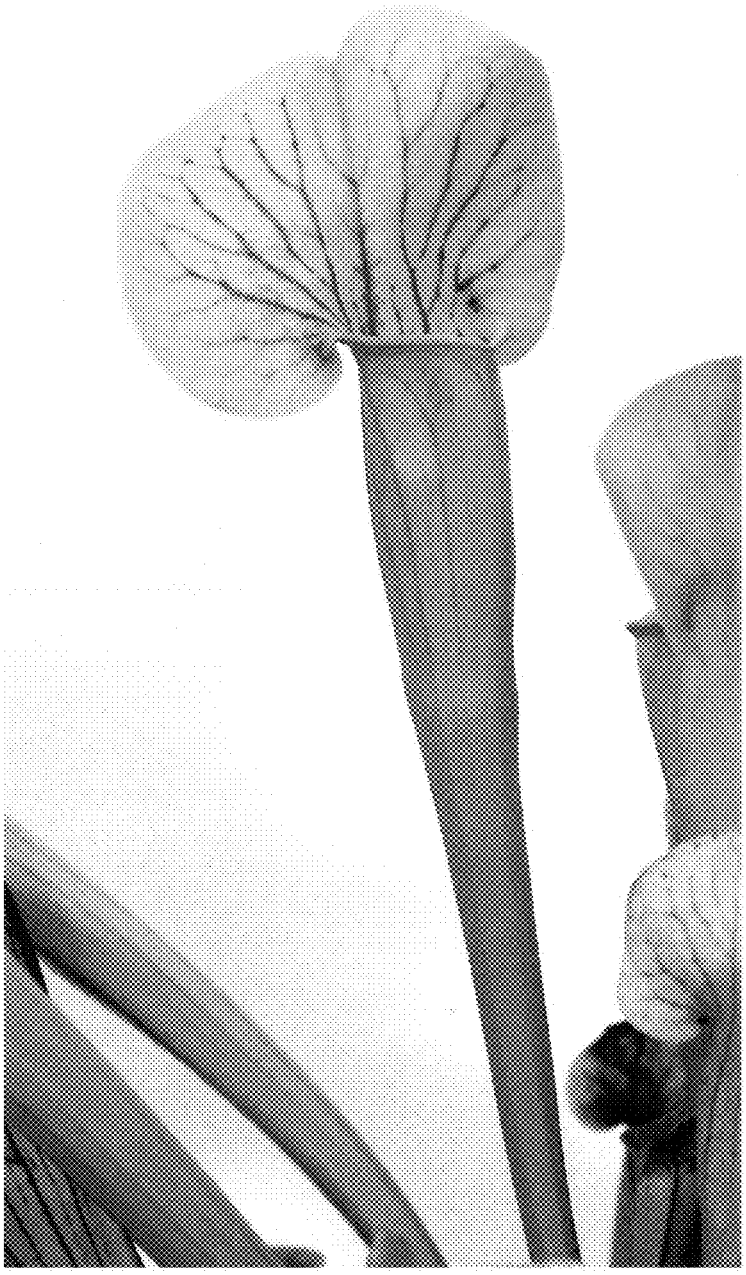
FIG. 2 illustrates an immature pitcher.
Figure 3:
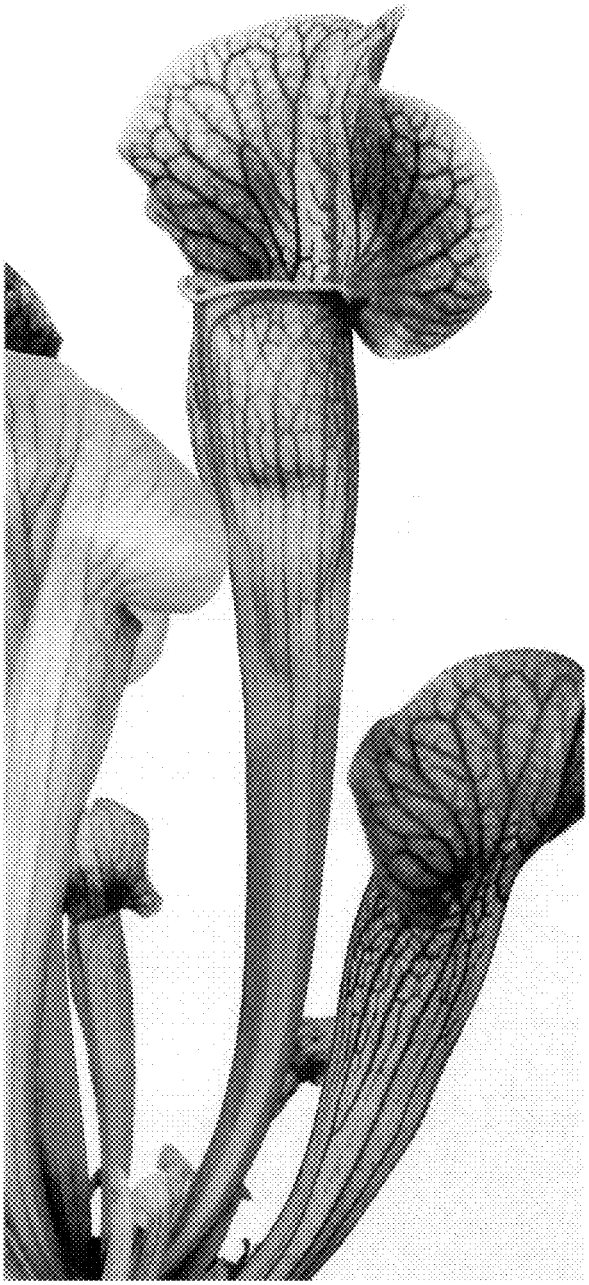
FIG. 3 illustrates a semi-mature pitcher.
Figure 4:
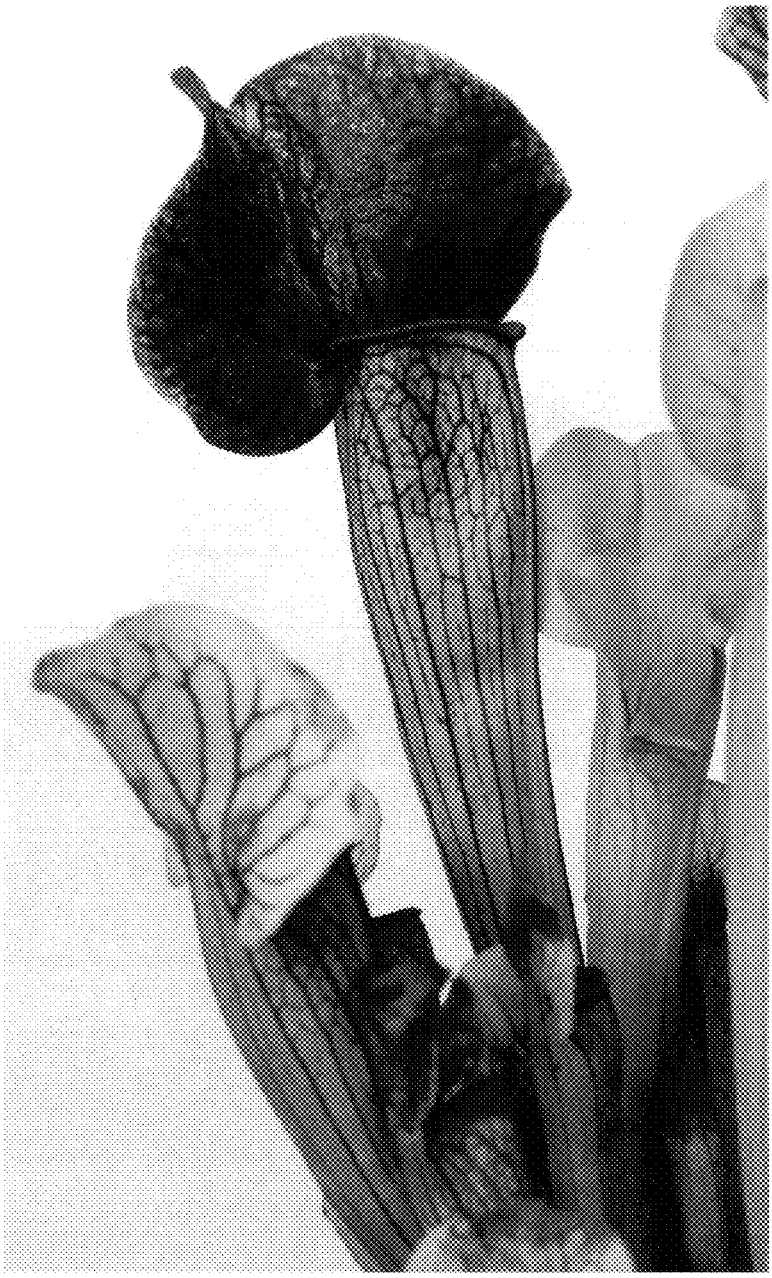
FIG. 4 illustrates a fully mature pitcher.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe '23CF101' plant is grown in a glass greenhouse in Aalsmeer, the Netherlands. The plant is approximately one year old in a 12-cm pot. Temperatures ranged between 21° C. to 35° C. during the day and 19° C. to 21° C. at night. No chemical treatments were given to the plants. Measurements and numerical values represent averages of typical plant types.

Botanical classification: *Sarracenia* hybrid '23CF101'.

PROPAGATION

Time to initiate rooting: 30 days at 24° C. in summer; 40 days at 20° C. in winter.

Root description: Moderately fine, not fleshy. Average diameter: 1 mm. Young roots herbaceous, mature roots slightly fibrous. Light to moderately dense, not freely branching. Colored RHS Greyed-Yellow 161A and 161B.

PLANT

Plant type: Perennial potted plant.

Growth habit: Upright, with epiascidiate leaves growing from a basal rosette.

Height: Approximately 28.2 cm.

Plant spread: Approximately 21.4 cm.

Growth rate: Moderate.

FOLIAGE

Leaf:

*Arrangement*.—Alternate, single, in basal rosette.

*Length*.—Average: 23.5 cm. Lower leaf zone (tube) average: 18.6 cm. Upper leaf zone (lid) average: 6.5 cm.

*Width*.—Lower leaf zone (tube) average diameter: 3.3 cm. Upper leaf zone (container) average: 8.7 cm.

*Shape*.—Leaf epiascidiate, typically consisting of a lower leaf zone, with a lamina rolled into a tube with a ventral wing and an upper leaf zone, formed as lid. Lower leaf zone shaped tubular, upper leaf zone (lid) shaped reniform.

*Aspect*.—Leaves in an average angle of 45° to horizontal, curled upward to 90° (near vertical) at the tip.

*Apex*.—Broad emarginate.

*Base*.—Tubular, fused.

*Margin*.—Lower leaf zone tubular, ventral wing entire. Upper leaf zone (lid) entire, coarsely undulate.

*Texture*.—Top surface: Lower leaf zone (tube) and upper leaf zone (lid): smooth, pubescent. Bottom surface: Lower leaf zone (tube) and upper leaf zone (lid): smooth, glabrous.

*Pubescence*.—Upper side of lower leaf zone (tube): Moderately covered with very short adpressed strigose hairs; average length: 0.5 mm, colored white; impossible to measure with RHS-CC due to small size. Upper leaf zone (lid): Moderately covered with very short adpressed strigose hairs; average length: 1.25 mm, colored near RHS White NN155D.

*Rugosity*.—Lower leaf zone (tube) and upper leaf zone (lid) non-rugose on both sides.

*Luster*.—Lower leaf zone (tube): Matte. Upper leaf zone (lid): Very slightly glossy.

*Color*.—

*Young foliage, upper side*.—Lower leaf zone (tube): RHS Yellow-Green 145A and 145B, fading to 145B towards the top. Veined Greyed-Orange N170A and N170B. Towards the top, lower leaf zone reticulately veined Greyed-Red 181A to 181C. Upper leaf zone (lid): RHS Yellow-Green 145A, reticulately veined Greyed-Red 181A to 181C.

*Young foliage, under side*.—Lower leaf zone (tube): RHS Yellow-Green 145A, fading slightly darker towards the top; a blend of 145A and 146D, base Greyed-Red 179A. Veined Greyed-Orange N170A and N170B, towards the top reticulately veined Greyed-Orange 174A and 174B. Upper leaf zone (lid): RHS Yellow-Green 145A, reticulately veined Greyed-Orange 173B, main vein nearest 171B.

*Semi-mature foliage, upper side*.—Lower leaf zone (tube): RHS Yellow-Green 144C, fading 145A towards the top; lower leaf zone reticulately veined Greyed-Purple 183B, 183C and 184B. Upper leaf zone (lid): RHS Yellow-Green 144B and 144C, moderately to strongly tinged Greyed-Orange 176A and 176B, and reticulately veined Greyed-Purple 187A.

*Semi-mature foliage, under side*.—Lower leaf zone (tube): RHS Yellow-Green, a blend of 144C and 146D, fading to 146D towards the top; base Red 53A to Greyed-Purple 185A. Veined Greyed-Orange 165B and 165C. Towards the top, reticulately veined Greyed-Orange 175A. Upper leaf zone (lid): RHS Yellow-Green 152A and 152B, margined Yellow-Green N144C, reticulately veined Greyed-Purple 183A.

*Mature foliage, upper side*.—Lower leaf zone (tube): RHS Yellow-Green 144C, fading to Greyed-Red 185B towards the top. Upper leaf zone (lid): RHS Yellow-Green N144D, very strongly tinged to near uniformly Greyed-Purple N186C and 187A.

*Mature foliage, under side*.—Lower leaf zone (tube): RHS Yellow-Green 144C, fading to 145A and 146D towards the top; base Red 53A. Upper leaf zone (lid): RHS Yellow-Green 144C, very strongly tinged to near uniformly Greyed-Orange 177A and 177B.

*Venation*.—Type: Reticulate. Color: Mature foliage, upper side: Lower leaf zone (tube): RHS Greyed-Purple N186C. Upper leaf zone (lid): RHS Greyed-Purple N186C. Mature foliage, under side: Lower leaf zone (tube): RHS Greyed-Purple 183A, fading to 187A towards the top. Upper leaf zone (lid): RHS Greyed-Purple N186C.

Other distinguishing characteristics: Lower leaf zone (tube) of epiascidiate leaves with a ventral wing, average length 17.1 cm, average width: 0.6 cm, texture and color similar to lower leaf zone (tube).

OTHER CHARACTERISTICS

Fruit/seed production: No fruits/seeds detected to date.

Temperature tolerance: Unknown, at least tolerant from −10° C. to 35° C.

USDA hardiness zones: USDA zones 4 to 9.

Tolerance to rain: High.

Tolerance to wind: Moderate.

Disease and pest resistance or tolerance: Neither resistant nor susceptible to normal diseases and pests of *Sarracenia*.

What is claimed is:

1. A new and distinct cultivar of *Sarracenia* plant named '23CF101' as herein illustrated and described.

* * * * *